United States Patent
Keller

(10) Patent No.: US 10,166,063 B2
(45) Date of Patent: Jan. 1, 2019

(54) DEVICE FOR DETECTING METAL WHEN BIOLOGICAL TISSUE IS ACTED ON BY MEANS OF A SPARKING ELECTROSURGICAL INSTRUMENT

(71) Applicant: ERBE ELEKTROMEDIZIN GMBH, Tuebingen (DE)

(72) Inventor: Sandra Keller, Hechingen (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 592 days.

(21) Appl. No.: 14/876,998

(22) Filed: Oct. 7, 2015

(65) Prior Publication Data

US 2016/0113702 A1    Apr. 28, 2016

(30) Foreign Application Priority Data

Oct. 23, 2014 (EP) .................................. 14190155

(51) Int. Cl.
*A61B 18/12* (2006.01)
*G01R 27/02* (2006.01)
(Continued)

(52) U.S. Cl.
CPC ........ *A61B 18/1233* (2013.01); *A61B 18/042* (2013.01); *G01R 19/165* (2013.01);
(Continued)

(58) Field of Classification Search
CPC . A61B 18/1233; A61B 18/1206; A61B 18/16; A61B 2018/1213;
(Continued)

(56) References Cited

U.S. PATENT DOCUMENTS 6,235,020 B1    5/2001 Cheng et al.
8,920,412 B2    12/2014 Fritz et al.
(Continued)

FOREIGN PATENT DOCUMENTS

CN    102368951 A    3/2012
CN    102599911 A    7/2012
(Continued)

*Primary Examiner* — Thomas Giuliani
(74) *Attorney, Agent, or Firm* — Blank Rome LLP

(57) ABSTRACT

A device for detecting metal with sparking electrosurgical instruments. The device contains a metal detector, which decides, on the basis of the current and voltage delivered to the instrument, whether a spark originating from the instrument contacts biological tissue or a metal part. The component of the current is determined that is inconsistent with a linear equivalent circuit. The elements of the linear equivalent circuit may be determined in a regression calculation. As first decision criterion, the spark characteristic variable $F_{rel}$ is determined from the current. As second decision criterion, a resistance characteristic variable R is determined, which characterizes the tissue resistance. Both characteristic variables are compared with threshold values. If the tissue resistance falls below the resistance threshold value and the spark characteristic variable exceeds the spark size threshold value, a signal is generated that characterizes the activation of the spark against a metal part.

9 Claims, 3 Drawing Sheets

(51) Int. Cl.
*G01R 19/165* (2006.01)
*A61B 18/04* (2006.01)
*A61B 18/00* (2006.01)

(52) U.S. Cl.
CPC .... *G01R 27/02* (2013.01); *A61B 2018/00589* (2013.01); *A61B 2018/00648* (2013.01); *A61B 2018/00666* (2013.01); *A61B 2018/00708* (2013.01); *A61B 2018/00827* (2013.01); *A61B 2018/00875* (2013.01); *A61B 2018/00892* (2013.01); *A61B 2018/1213* (2013.01)

(58) Field of Classification Search
CPC ........... A61B 2018/00892; A61B 2018/00827; A61B 2018/00875; A61B 2018/00648; A61B 2018/00589; A61B 2018/00708; A61B 2018/00666; A61B 2018/00636; A61B 2018/00642; A61B 5/06; G01R 27/02; G01R 19/165
USPC ................................................ 606/34, 35, 38
See application file for complete search history.

(56) References Cited

U.S. PATENT DOCUMENTS

2006/0219682 A1* 10/2006 Klett .................. A61B 18/1206
                                                                219/130.4
2012/0215213 A1*  8/2012 Juzkiw .................. A61B 18/14
                                                                606/33

FOREIGN PATENT DOCUMENTS

| DE | 10 2004 010 769 A1 | 9/2005 |
| EP | 1 849 425 A1 | 10/2007 |
| JP | 08-196543 A | 8/1996 |
| JP | H 9-154850 A | 6/1997 |
| JP | 2001-520081 A | 10/2001 |
| JP | 2006-289061 A | 10/2006 |
| JP | 2010-534527 A | 11/2010 |
| JP | 2012-125571 A | 7/2012 |
| JP | 5465243 B2 | 4/2014 |
| WO | WO 97/45157 A1 | 12/1997 |

* cited by examiner

DEVICE FOR DETECTING METAL WHEN BIOLOGICAL TISSUE IS ACTED ON BY MEANS OF A SPARKING ELECTROSURGICAL INSTRUMENT

TECHNICAL FIELD

Embodiments of the invention relate to a device for detecting foreign bodies, in particular metal foreign bodies, in biological tissue when this is acted on by means of electrosurgical instruments that generate electrical discharges.

BACKGROUND

Electrosurgical instruments that use an electrical discharge taking place in a fluidic medium in order to act on biological tissue are known in principle. Such instruments for example include argon plasma coagulation instruments, which generate a spark burning in argon atmosphere or a plasma jet, or sparking scalpels or the like. Monopolar and bipolar resection instruments are known which, in non-conductive (Purisole) or conductive (saline solution) liquid, heat the liquid such that the liquid evaporates and sparks to the tissue or a further electrode form in this vapour. When handling argon plasma coagulation instruments, particular care must be taken when foreign bodies, in particular metal foreign bodies, are present in the biological tissue. These bodies may be, for example, stents or other metal parts, which have been implanted already in a patient in the past or which have been implanted during the current intervention. If the spark or plasma acts unintentionally on a stent, a metal clamp or another metal body in the biological tissue, this may cause damage to the metal part, whereby said metal part may lose its function. The surrounding tissue may also be damaged undesirably, for example on account of heat conduction.

On the other hand there are cases in which it is desirable for the spark or plasma to act on the metal foreign body, for example in order to shorten a stent or to perform certain surgical interventions. These include, for example, the coagulation of a bleeding vessel by means of anatomical tweezers, heated selectively by the spark or plasma jet of the electrosurgical instrument and thus capable of coagulating the vessel.

It is also known, for the application of monopolar and bipolar resection loops in the case of TUR, that too short a distance between the resection loop and the resectoscope unintentionally results in sparking onto the metal resectoscope. This undesirable sparking leads to a flow of current through the metal resectoscope. Since the resectoscope is in turn in contact with the biological tissue, this results in undesirable coagulation effects on the tissue.

An object is therefore to create a concept with which the action of a sparking electrical instrument on metal can be reliably differentiated from the action of the instrument on biological tissue.

SUMMARY

The device according to an embodiment of the invention may belong to an electrosurgical instrument or may be part thereof. It may equally belong to a generator intended to feed power to the instrument or may be part of such a generator. Alternatively, the device may be arranged as a separate module between the generator and the electrosurgical instrument.

The device includes a measuring device for measuring a voltage provided by the generator for operation of the instrument and for measuring the current delivered from the generator to the instrument. If the internal resistance of the generator is low or zero and the output voltage is known, it is possible to also dispense with the measurement of the voltage; it is then sufficient to measure the current. The current (and the voltage) can be measured continuously or intermittently, for example at short intervals. The voltage and the current are preferably measured at short intervals. If the generator delivers an alternating voltage in order to feed the electrosurgical instrument, preferably an HF alternating voltage, the intervals are preferably shorter than half the period length of the voltage or of the current. When measuring the voltage or the current, at least one suitable characteristic value of the voltage and of the current is measured. Such a characteristic value may be the momentary value, the peak value, the mean value, the effective value or another value suitable for characterisation.

The metal detector belonging to the device is configured to decide, on the basis of the current and on the basis of the voltage, i.e. ultimately on the basis of one or more characteristic values for the current and also one or more characteristic values for the voltage, whether a spark originating from the instrument contacts biological tissue or a metal part.

With this device the user can reliably identify in good time when a metal part is acted on by a spark or plasma, even when visibility conditions are poor. It is possible to connect the metal detector to a signalling device in order to provide the user with a suitable, for example haptic, optical or acoustic signal so that the user identifies metal contact by the plasma or the spark. It is also possible to use a signal generated by the metal detector to switch off the generator or to control said generator in another way. For example, the output of the generator may be reduced in the event of metal detection so as to avoid undesirable biological effects. If, by contrast, it is desired to act on the metal, the signal can be used not to switch off the generator, but to increase the output thereof when contact of metal by the spark or the plasma is identified, for example so as to assist the cutting of metal by means of spark or plasma.

The metal detector may contain an analysis device, which determines a resistance characteristic variable and a spark characteristic variable. The resistance characteristic variable is a value dependent on the tissue resistance. The spark characteristic variable is preferably a variable dependent on the spark size. Both characteristic variables, i.e. the resistance characteristic variable and the spark characteristic variable, can be compared with corresponding threshold values in order to generate a meaningful signal from this comparison. Metal contact by the plasma or the spark is preferably then signalled when the electrical resistance characteristic variable, i.e. the resistance characteristic value, falls below the resistance threshold value and the spark characteristic variable, i.e. the spark characteristic value, exceeds the spark size threshold value. Other situations can be associated with all other combinations:

The resistance characteristic value falls below the resistance threshold value and the spark characteristic variable is lower than the spark size threshold value. There is direct contact between the electrode of the instrument and the tissue.

If the resistance characteristic variable is greater than the resistance threshold value, but the spark size is below the spark size threshold value, there is no spark or the spark shoots into the air.

The resistance characteristic variable is greater than the resistance threshold value and at the same time the spark characteristic variable is greater than the spark size threshold value—the spark or plasma influences the tissue without metal contact.

In order to calculate or otherwise determine the resistance characteristic variable and the spark characteristic variable, all suitable methods can be used. By way of example, the resistance characteristic variable can be fixed as the linear component of the electrical resistance, which is given as the quotient of a characteristic value for the measured current and of a characteristic value of the measured voltage. In particular, the quotient can be formed from the effective values of current and voltage and then multiplied by the power factor in order to form the resistance characteristic variable. This resistance characteristic variable contains not only the tissue resistance. Rather, further components, for example the line resistance of the feed line of the instrument and where applicable also linear resistance components from the spark, are also included. However, the resistance characteristic variable thus determined is a good measure for the tissue resistance.

The non-linear component of the current, which decisively drops to the non-linear resistance formed by the spark, can be determined in order to determine the spark characteristic variable. For this purpose the analysis device may be configured to calculate the associated current $i_{sim}(t)$ on the basis of a linear equivalent circuit and the measured voltage (or the corresponding characteristic value of the voltage). The difference $i_f(t)$ between the calculated current $i_{sim}(t)$ and the measured current $i(t)$ characterizes the current produced by the non-linearity of the spark. The ratio from the effective value $F_{eff}$ of this difference $i_f(t)$ and the effective value $i_{eff}$ of the measured current $i(t)$ can be used as spark characteristic variable $F_{rel}$.

Instead of the comparison of the resistance characteristic variable with the resistance threshold value and the comparison of the spark characteristic variable with the spark size threshold value, it is also possible to examine the resistance characteristic variable and the spark characteristic variable for rapid changes over time. If the gradient of the rise of the spark characteristic variable $dF_{rel}/dt$ and of the rise of the resistance characteristic variable $dR/dt$ in each case exceeds a certain limit value f0, r0, metal contact can be determined in turn.

Further details of embodiments of the invention are the subject matter of the drawing, the description, or claims.

DETAILED DESCRIPTION

Figure 1:
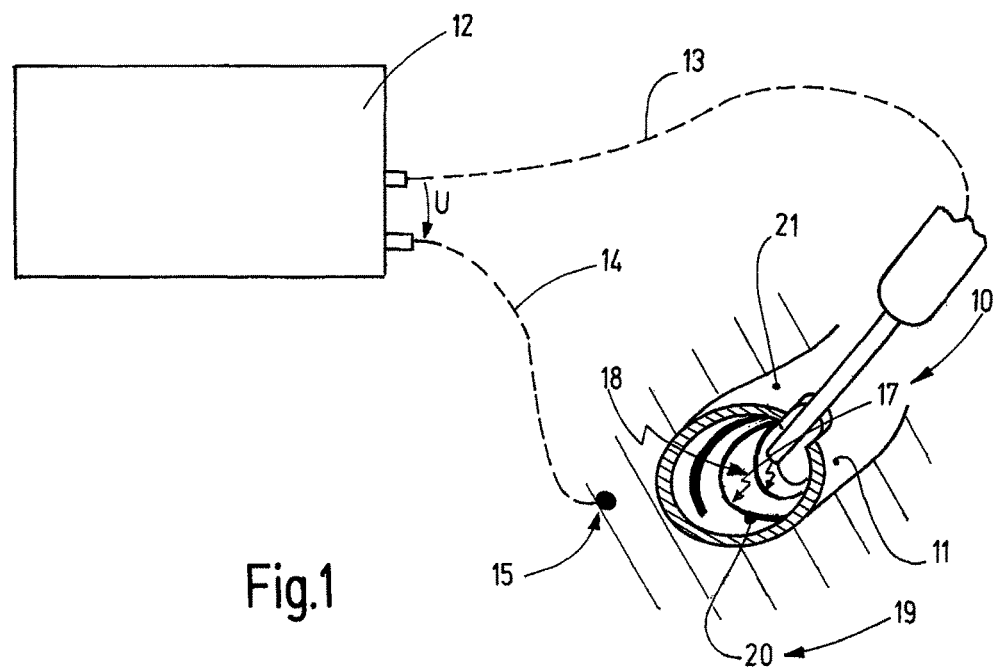
FIG. 1 shows a schematic illustration of an embodiment of a sparking, electrosurgical instrument fed by a generator when acting on biological tissue.

FIG. 1 schematically illustrates a situation of use, in which a treatment is carried out on biological tissue 11 by means of an electrosurgical instrument 10. The instrument 10 is for this purpose supplied with electrical current by an apparatus 12. The voltage u provided by the apparatus 12 and also the current i delivered to the instrument 10 are preferably periodic variables with a frequency of preferably several 100 kHz, for example 350 kHz. Although the present invention is not limited to this, it is suitable in particular for some monopolar applications. A first line 13 accordingly leads from the apparatus 12 to the instrument 10. A second line 14 leads from the apparatus 12 to a large-area neutral electrode 15 attached to the undamaged surface of the tissue 11, in particular the skin of the patient.

The instrument 10 has at least one electrode 17, from which a current flow to the biological tissue 11 starts. Depending on the actual situation, the current can flow by direct tissue contact or via a spark 18, which sparks over between the electrode 17 and the biological tissue 11. Here, depending on the application in question, the spark 18 may cross a volume containing air and/or water vapour and/or vapour of other liquids, such as Purisole, saline solution and/or another gas, such as nitrogen, carbon dioxide or noble gas, in particular such as argon. The gas or gas mixture or vapour present ionises in the region of the spark 18 and forms a plasma, wherein the spark contacts the biological tissue 11 and introduces current thereinto.

The biological tissue 11 may contain electrically conductive foreign bodies, in particular metal parts 19, in particular such as stents 20 (FIG. 1) for holding open hollow vessels 21 such as the esophagus or the like. The metal part 19 may additionally be a clamp, a screw, a plate, a wire or another component introduced into the body of a patient.

When treating the biological tissue 11 it may be that the spark 18 contacts metal parts 19. Such a contact should in no way occur in an uncontrolled manner. It may be desirable for example to heat or to cut metal parts selectively, for example in order to shorten stents or to heat surgical tweezers, for example in order to produce tissue coagulation between the branches of the tweezers. It may also be undesirable, however, for example when a heating of metal parts 19 leads to damage thereof and also to damage of surrounding biological tissue. With a poor view of the area of use, it is sometimes difficult however for the user to detect metal parts in good time. In particular, it may be difficult however to detect the contact of the metal parts 19 by the spark 18 quickly enough.

Figure 2:
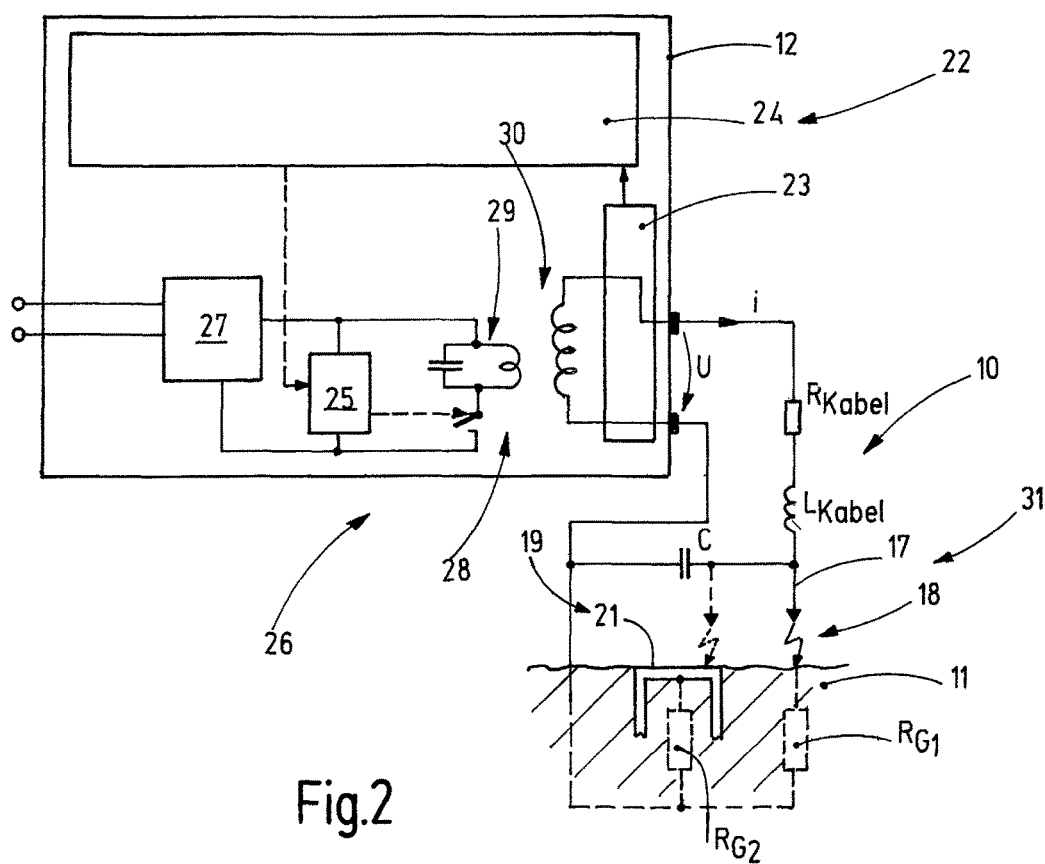
FIG. 2 shows a circuit diagram of components of an embodiment of the generator of the instrument and of the biological tissue.

In order to detect metal contact by the spark 18, a metal detector 22 is provided, which, as illustrated in FIG. 2, may be part of the apparatus 12 or alternatively also part of the instrument 10 or may be formed as an intermediate module. Such an intermediate module is to be connected instead of the lines 13, 14 to the apparatus 12, wherein the lines 13, 14 are then attached to the intermediate module.

A measuring device 23 may belong to the metal detector 22 and measures the voltage u provided for the instruments 10 and also the current i delivered to the instrument 10. Here, it measures at least one characteristic value Ku of the voltage and at least one characteristic value Ki of the current. Such a characteristic value Ki of the current may be the instantaneous value i(t) of the peak value $i_{peak}$, of the mean value $i_{mean}$, of the effective value $i_{eff}$ or another value suitable for characterisation. Such characteristic values can be measured continuously or in a sampled manner. When sampling instantaneous values, sampling is preferably performed with more than double the frequency of the current (for example with more than 700 kHz). The instantaneous value u(t), the peak value $u_{peak}$, the mean value $u_{mean}$, the effective value $u_{eff}$ or another value suitable for characterisation may equally be measured as characteristic value Ku for the voltage. The measurement can be performed continuously or periodically. When sampling the instantaneous value, sampling is performed preferably with more than double the frequency of the voltage. Where reference is made below and above to the "measuring of the current" or "measuring of the voltage", this refers to the explained measurement of a corresponding characteristic value of the current or of the voltage.

The measured characteristic values Ku, Ki for the voltage and the current are transferred from the measuring device 23 to an analysis device 24. The analysis device serves to distinguish, on the basis of the characteristic variables for the current and the voltage, whether the spark 18 is in contact with the tissue 11 or with the metal part 19.

The analysis device 24 can be connected subsequently to a controller 25 of a generator 26, which is illustrated schematically in FIG. 2 and serves to feed high-frequency electrical energy to the instrument 10. The generator 26 typically comprises, besides the control device 25, a power supply 27 and a power oscillator 28 connected thereto comprising a resonating circuit 29 and a potential-free HF decoupling coil 30. The controller 25 controls the operation of the generator 26, i.e. activate and deactivate the generator, and defines the voltage and/or the current and/or the output and/or the crest factor. The controller 25 can communicate with operation members not illustrated in greater detail, which are formed as switches or setting devices on the apparatus 12 and/or the instrument 10 and/or as further separate switches or input devices.

In order to detect whether the spark 18 contacts the tissue 11 or the metal part 19 on the basis of the measured current and the measured voltage, the analysis device 24 is configured to determine at least two characteristic variables, specifically a spark characteristic variable $F_{rel}$ and a resistance characteristic variable R. As spark characteristic variable $F_{rel}$, a characteristic variable is preferably selected that characterizes the size and/or the intensity of the spark 18. By way of example, a characteristic variable that characterizes the non-linearity of the electric network formed by the instrument 10, the spark 18 and the biological tissue 11 can be used as spark characteristic variable $F_{rel}$. The electric network thus formed is illustrated in simplified form in FIG. 2. This network includes the ohmic resistance $R_{Kabel}$ of the lines 13, 14, the inductance $L_{Kabel}$, the capacitance C to be measured between the lines 13, 14, and the tissue resistance $R_{G1}$ or $R_{G2}$. The tissue resistance $R_{G1}$ is the resistance of the biological tissue when the spark 18 contacts this tissue. The tissue resistance $R_{G2}$ is the typically lower tissue resistance given by the current distribution of the metal part 19 when the spark 18 contacts this tissue. The network also includes the non-linear resistance of the spark 18.

Figure 3:
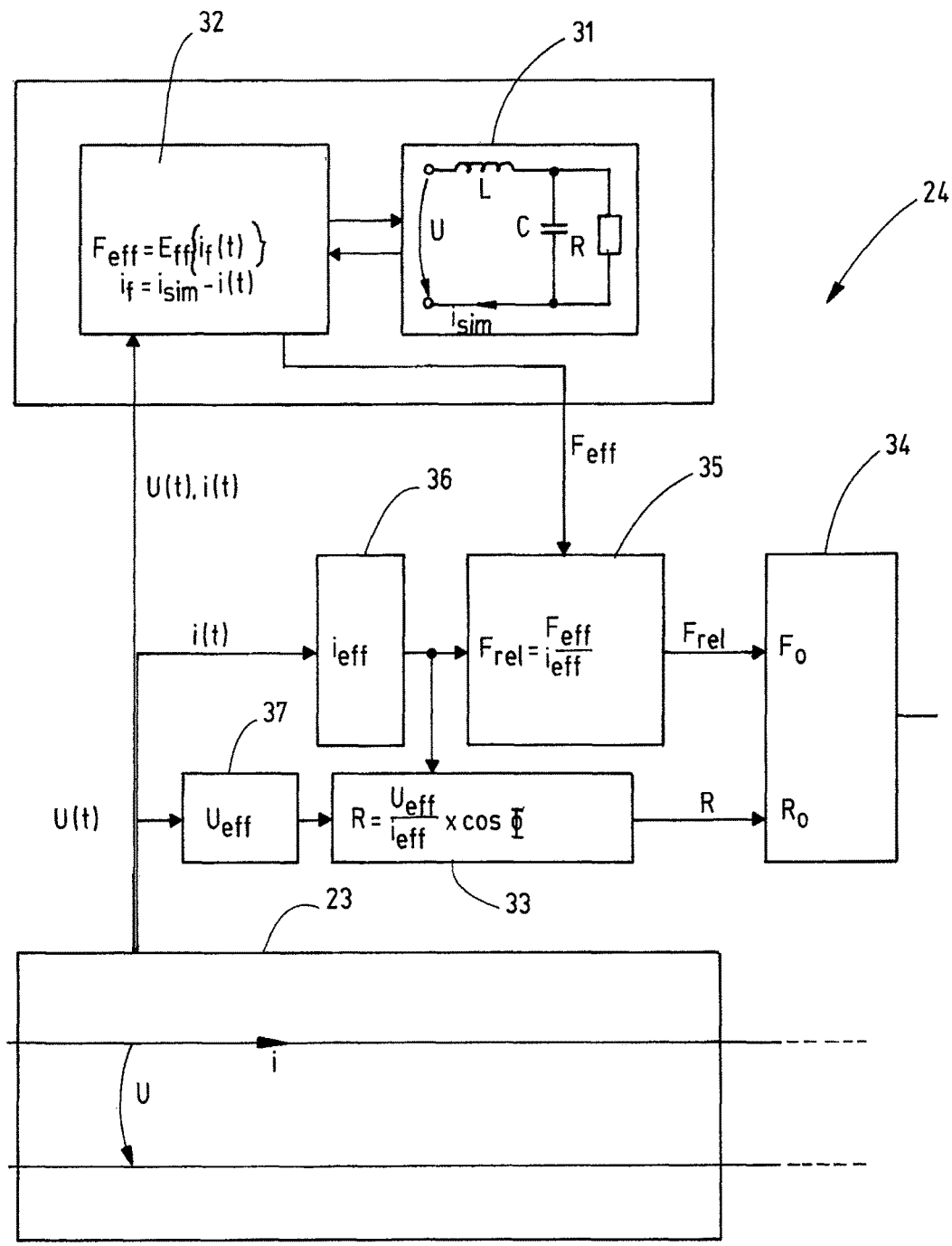
FIG. 3 shows a block diagram of an embodiment of the device for metal detection.

The analysis device 24 may have an internal equivalent circuit 31, i.e. an internal network model 31 of this electric network, as indicated in FIG. 3. The network model 31 may be a simplified representation of the network actually provided in accordance with FIG. 2, in which the inductances, capacitances and resistances occurring are combined to give elements R, L and C. Depending on whether the network currently behaves predominantly inductively or predominantly capacitively, a simplified network model 31a or 31b in accordance with FIG. 4 or FIG. 5 can be selected instead of the network model 31. The selection can be made and decided by the analysis device on the basis of the lag or lead of the current i relative to the voltage.

The analysis device 24 is designed to firstly determine the values of the elements L, R, C of the network model 31, 31a, 31b. For this purpose, the values of the elements L, R, C are defined for example within the scope of a regression calculation or by means of the method of the smallest error square, such that the currents and voltages occurring mathematically in the network model 31, 31a, 31b are adapted as best as possible to the current actually measured and to the voltage actually measured. Since the ohmic line resistance $R_{Kabel}$ is mostly less than 1 ohm, this is insignificant. The value R of the resistance in accordance with the network model 31a,b according to FIG. 4 or 5 thus corresponds to the tissue resistance. The components of the current i and of the voltage u not reconciling with the linear network model are assigned to the non-linear resistance F of the spark 18. The values of the elements L, R, C may be determined at the start of an activation or at intervals or continuously.

As indicated in FIG. 3, the spark characteristic variable $F_{rel}$ can be determined from the actual current i(t) and the current $i_{sim}(t)$ defined by the linear network. FIG. 3 illustrates, for this purpose, a plurality of blocks for explaining the processing of the measured current i(t) and of the voltage u(t). These blocks can be produced by program codes or otherwise. The assignment of functions to blocks is purely exemplary and may also be different.

Figure 4:
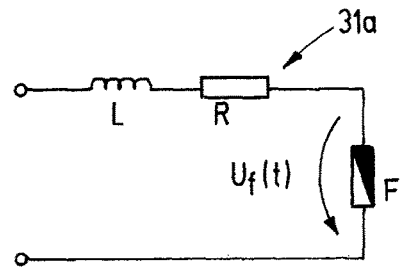
FIGS. 4 and 5 show embodiments of equivalent circuits of the device according to FIG. 3.
Figure 5:
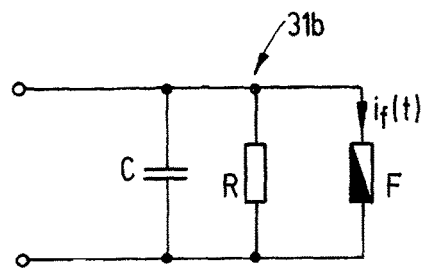

A block 32 determines sporadically, periodically or continuously the elements R, L and/or C of the network model 31 according to FIG. 3, 4 or 5. The network model 31 then calculates, with the input of the measured voltage u(t), a current $i_{sim}(t)$ and the difference thereof $i_f(t)$ from the measured current i(t) and the effective value $F_{eff}$ thereof from $i_f(t)$. The current $i_{sim}(t)$ does not match the effective value $i_{eff}$ of the measured current i(t) particularly when the spark 18 has ignited.

The current error $i_f(t)$ is calculated as the difference of the target current $i_{sim}(t)$ calculated from the equivalent circuit according to FIG. 4 or 5 for the HF-surgical application and of the HF current i(t) measured during the HF application:

$$i_f(t)=i_{sim}(t)-i(t)$$

The block 32 calculates the deviation of the simulated current $i_{sim}(t)$ from the measured current i(t) as current error $i_f(t)$. Alternatively, $i_f(t)$ can also be calculated on the basis of the instantaneous values of the target current $i_{sim}(t)$ and of the actual current i(t). $F_{eff}$ is the effective value of the current error $i_f(t)$:

$$F_{eff} = \sqrt{\frac{1}{T} \cdot \int_T i_f^2(t)}$$

and is calculated in block 32.

The current error $i_f(t)$ is maximal when the measured HF current i(t) deviates maximally from the calculated regression current. This deviation occurs particularly in HF-surgical applications with sparking, in which case there is a strong distortion of the HF current i(t) on account of the sparking. In the case of the sparking and the associated distortion of the current, the non-linear component of the equivalent circuit for calculation of the regression current is particularly high. The linear elements of the equivalent circuit according to FIGS. 3 to 5 cannot fully explain the measured HF current i(t) and lead to a regression current $i_{sim}(t)$ deviating from the measured HF current i(t). This correlates with a high current error $i_f(t)$, whereby the effective spark characteristic value $F_{eff}$ rises accordingly. By forming a ratio using the measured effective HF current $i_{eff}$, a relative measure for the sparking is obtained in the block 35.

The analysis device 24 calculates, as explained above, the linear values of the network model 31 according to FIG. 3 or 31a or b according to FIG. 4 or 5 on the basis of the regression analysis. The ohmic component R can be used as resistance characteristic variable and primarily characterizes the resistance of the biological tissue 11, i.e. in the illustration according to FIG. 2 is to be assigned to the tissue resistances $R_{G1}$ or $R_{G2}$. The regression calculation is for this purpose performed continuously by the block 32, i.e. the regression block, in order to determine the instantaneous resistance characteristic variable R during the entire operation of the instrument 10.

Alternatively, the tissue resistance can also be determined by a separate resistance calculation block as illustrated in FIG. 3. For this purpose the blocks 36, 37 initially determine the effective values of the HF voltage and of the HF current $u_{eff}$ and $i_{eff}$ from the instantaneous values i(t), and also determine the power factor cos Φ. (Alternatively the resistance calculation block 33 can also obtain these effective values from the measuring device 23). As resistance characteristic variable, the resistance calculation block 33 forms the quotient of the effective value $u_{eff}$ of the HF voltage u(t) and of the effective value $i_{eff}$ multiplied by the power factor cos Φ.

Figure 6:
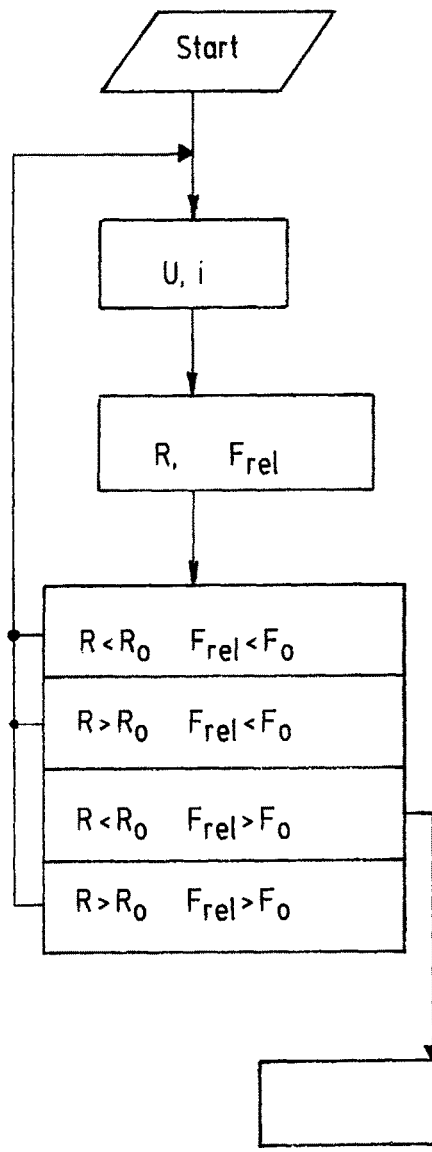
FIG. 6 shows a flow diagram for an embodiment of the metal detection on the basis of resistance threshold value and spark size threshold value.

A comparator 34 compares the spark characteristic variable $F_{rel}$ determined in the block 35 with a spark size threshold value $F_0$. In addition, the comparator compares the resistance characteristic variable R with a resistance threshold value $R_0$. FIG. 6 illustrates the process. The spark characteristic variable $F_{rel}$ may be above or below the spark size threshold value $F_0$. The resistance characteristic variable R may also be above or below the resistance variable threshold value $R_0$. Four possible constellations are provided as a result. It has been found that, with a suitable choice of $R_0$ of, for example, 300 ohm and of $F_0$ of, for example, 0.4, the contacting of metal by the spark 18 is then confirmed when the resistance characteristic variable R is below the resistance threshold value $R_0$ and the spark characteristic variable $F_{rel}$ is above the spark size threshold value $F_0$. With the other three constellations other situations are present, for example contact between instrument 10 and tissue 11 without sparking, activation of the electrode 17 in air without ignited spark, or spark to the tissue 11 with sparking. If, by contrast, a spark ignited against a metal part is detected, a branch is made to a block 38, which symbolises an appropriate measure. Such a measure may be the sending of a perceptible signal or an influencing of the controller 25. This, for example, may reduce or increase the output or may switch off the generator 26, change the crest factor, or similar.

Figure 7:
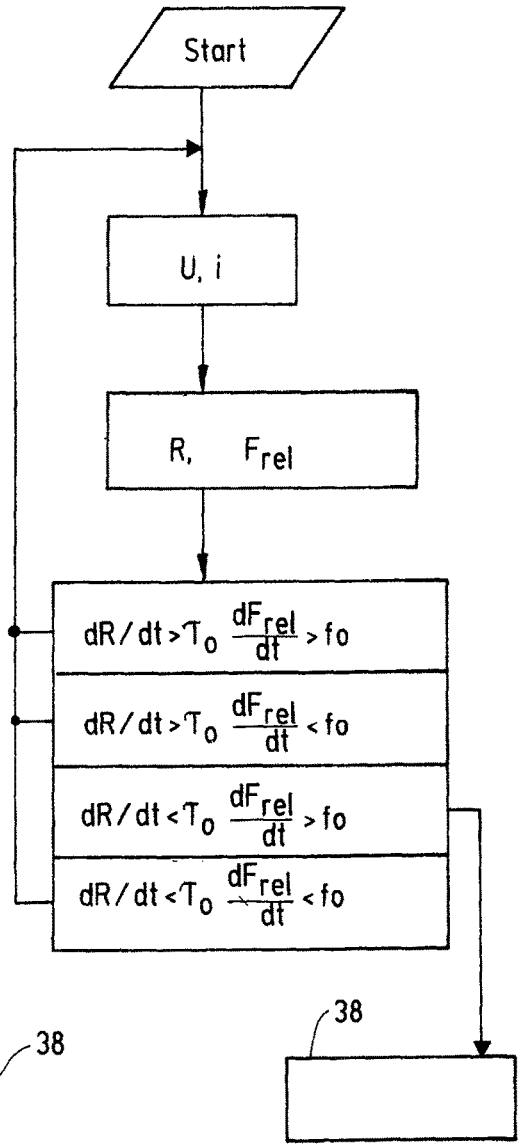
FIG. 7 shows a flow diagram for an embodiment of the metal detection on the basis of the change over time of the resistance characteristic variable and the spark characteristic variable.

FIG. 7 illustrates a modified embodiment of the method. The resistance characteristic variable R and the spark characteristic variable $F_{rel}$ are determined, again continuously, as described above. By contrast with the method described above, however, these are not compared with absolute threshold values $F_0$ and $R_0$. Rather, the change over time $dR/dt$ of the resistance characteristic variable R and the change over time $dF_{rel}/dt$ of the spark characteristic variable $F_{rel}$ is determined as evaluation criterion and compared with limit values $r_0$ and $f_0$. A branch is again then made to the measure block 38 when the change $dR/dt$ of the tissue resistance is below a resistance change threshold value $r_0$ and the change $dF_{rel}/dt$ of the spark characteristic variable $F_{rel}$ is above a spark size change threshold value $f_0$. It is thus possible to avoid false conclusions with regard to metal contact as a result of random measured value fluctuation.

A device according to an embodiment of the invention for metal detection with sparking electrosurgical instruments 10 contains a metal detector 22, which decides on the basis of the current i(t) (and also the voltage) delivered to the instrument 10 whether a spark 18 originating from the instrument 10 contacts biological tissue 11 or a metal part 19. This is preferably implemented by determining the component of the current i(t) that is inconsistent with a linear equivalent circuit 31. The elements of the linear equivalent circuit 31 are determined previously or during the operation in a regression calculation. As first decision criterion, the spark characteristic variable $F_{rel}$ is determined from the current i(t). As second decision criterion, a resistance characteristic variable R is determined, which characterizes the tissue resistance. Both characteristic variables are compared with threshold values $F_0$, $R_0$. If the tissue resistance R falls below the resistance threshold value $R_0$ and if the spark characteristic variable Frel exceeds the spark size threshold value $F_0$, a signal is generated, which characterizes the activation of the spark 18 against a metal part 19.

What is claimed as new and desired to be protected by Letters Patent of the United States is:

1. A device for detecting metal when biological tissue is acted on by means of a sparking electrosurgical instrument, the device comprising:
   a measuring device for measuring a voltage provided by a generator for operation of the instrument and measuring a current delivered from the generator to the instrument; and
   a metal detector configured to decide, on the basis of the current and the voltage, whether a spark originating from the instrument contacts biological tissue or a metal part, the metal detector comprising:
      an analysis device for determining a resistance characteristic variable dependent on a tissue resistance and a spark characteristic variable dependent on a spark size; and
      a comparator for comparing the resistance characteristic variable with a resistance threshold value and the spark characteristic variable with a spark size threshold value, wherein the comparator is configured to indicate contact of metal by the spark originating from the instrument when the resistance characteristic variable falls below the resistance threshold value and the spark characteristic variable exceeds the spark size threshold value.

2. The device of claim 1, wherein the generator is an HF generator.

3. The device of claim 1, wherein the measuring device is configured to determine at least one characteristic value of current and voltage continuously.

4. The device of claim 3, wherein the at least one characteristic value of current and voltage is selected from the group consisting of instantaneous value, peak value, mean value and effective value.

5. The device of claim 1, wherein the measuring device is configured to determine a power factor for multiplying a quotient of current and voltage to form the resistance characteristic variable.

6. A device for detecting metal when biological tissue is acted on by means of a sparking electrosurgical instrument, the device comprising:

a measuring device for measuring a voltage provided by a generator for operation of the instrument and measuring a current delivered from the generator to the instrument; and a metal detector configured to decide, on the basis of the current and the voltage, whether a spark originating from the instrument contacts biological tissue or a metal part, the metal detector comprising:

an analysis device for determining a resistance characteristic variable dependent on a tissue resistance and a spark characteristic variable dependent on a spark size; and a comparator for comparing the resistance characteristic variable with a resistance threshold value and the spark characteristic variable with a spark size threshold value, wherein the comparator is configured to indicate contact of metal by the spark originating from the instrument when the resistance characteristic variable falls below the resistance threshold value and the spark characteristic variable exceeds the spark size threshold value, wherein the analysis device is configured to determine the spark characteristic variable on the basis of the non-linear component of the current.

7. The device of claim 6, wherein the analysis device is configured to determine an estimated value for the non-linear component of the current.

8. The device of claim 7, wherein the analysis device is configured to determine the estimated value for the non-linear component of the current on the basis of a deviation of the measured current from a current calculated on the basis of a linear equivalent circuit.

9. The device of claim 8, wherein the analysis device is configured to determine values of elements of the linear equivalent circuit from the measured current and the measured voltage.

* * * * *